United States Patent [19]

Knox et al.

[11] Patent Number: 4,927,669

[45] Date of Patent: May 22, 1990

[54] OIL FIELD CORROSION INHIBITION

[75] Inventors: David E. Knox, Goose Creek; Eugene R. Fischer, James Island, both of S.C.

[73] Assignee: Westvaco Corporation, New York, N.Y.

[21] Appl. No.: 219,184

[22] Filed: Jul. 15, 1988

[51] Int. Cl.$^5$ ............................................. B05D 7/22
[52] U.S. Cl. .................................. 427/239; 427/230; 427/384; 427/388.1
[58] Field of Search ..................... 427/239, 388.1, 384, 427/230

[56] References Cited

U.S. PATENT DOCUMENTS

| | | | |
|---|---|---|---|
| 3,919,453 | 11/1975 | Bussell | 427/388.4 |
| 4,505,954 | 3/1985 | Hokamura et al. | 427/407.1 |
| 4,508,767 | 4/1985 | Hokamura et al. | 427/407.1 |
| 4,514,445 | 4/1985 | Hokamura et al. | 427/407.1 |

*Primary Examiner*—Janyce Bell
*Attorney, Agent, or Firm*—Terry B. McDaniel; Richard L. Schmalz

[57] ABSTRACT

An inhibitor formulation including the product obtained by reacting maleic anhydride or fumaric acid with fatty acids containing unsaturation in the presence of a suitable catalyst, such as iodine, clay, or silica, is disclosed to provide improved corrosion inhibition in oil field equipment and piping over conventional dimer/trimier based inhibitor formulations.

9 Claims, No Drawings

OIL FIELD CORROSION INHIBITION

BACKGROUND OF THE INVENTION

(1) Field of the Invention

This invention relates to inhibiting corrosion of metals in oil field applications where hydrocarbons and water are being taken from producing wells. Water may, of course, lead to corrosion of metal piping, etc., which is used in downwell applications. It is, therefore, necessary to add a suitable agent to the oil/water medium to effectively reduce or eliminate problems which are associated with corrosion of metallic parts. Failure to do so results in extensive corrosion of metal in the field leading to expensive repairs and lost productivity.

(2) Description of the Prior Art

Currently employed formulations which are effective in reducing corrosion in oil well piping consist of materials which are produced by the thermal condensation of functionalized C-18 fatty acids (containing one or two double bonds, e.g. oleic and linoleic, respectively). Examples of the methods by which the thermal polymerization of fatty acids occurs include heating an appropriate fatty acid, e.g., tall oil fatty acid or soya fatty acid, in the presence of a clay or other suitable catalyst to give varying amount of C-36 (dimerized) and C-54 (trimerized) fatty acid. This produces a material which when used in the oil field applications provides reasonable protection to the metals present. High molecular weight has been of presumed importance in attaining film persistency due to the nature of the molecule, i.e., multiple bonding sites and a large fatty backbone. For instance, dimer/trimer mixes perform considerably better than their monomeric counterparts. Normally, when the dimer/trimer mixtures are employed they are co-formulated with materials such as fatty acid imidazolines and certain oils. This maximizes performance in the materials to a great degree. Although there is a considerable history of use of dimer/trimer formulations, there is still a considerable call for materials which show a better cost performance profile than those materials currently in use.

SUMMARY OF THE INVENTION

It has been discovered that improved oil field corrosion inhibition may be achieved by employing in the inhibitor formulation the product obtained by reacting maleic anhydride or fumaric acid with fatty acids containing unsaturation in the presence of a suitable catalyst, such as iodine, clay, or silica. This material, unexpectedly, gives improved film persistency and corrosion inhibition over corresponding dimer/trimer mixes. This is surprising since the molecular weight of the maleinized adduct is considerably lower than that of either dimer or trimer acids. Thus, contrary to conventional wisdom, molecular weight is not a prerequisite to the attainment of excellent film persistency. Furthermore, it has been discovered that these materials perform well under conditions of both "sweet" ($CO_2$) and "sour" ($H_2S$) down hole environments enabling use under either set of conditions. For all formulations tested, our acid-anhydrides have been found to have equivalent inhibition compared with dimer/trimer mixes under constant concentration testing. This less rigorous testing procedure (vs. film persistency) does not discriminate between current products and our new materials.

Not only do these corrosion inhibitors perform equivalent to dimer/trimer mixes, but in fact perform considerably better than these higher molecular weight materials under conditions of testing. As a result, the amount of inhibitor needed to obtain the desired amount of corrosion inhibition is between three times and five times less than that required for those materials which contain dimer/trimer mixes. Typically, under normal testing procedures between 2,000 and 30,000 ppm inhibitor are required to give effective protection when dimer/trimer mixes are used at 5% salt solution. At 10% salt solution, the required concentration of dimer/trimer mixes is greater yet with the anhydride doses essentially constant and dimer/trimer requiring in excess of 40,000 ppm to attain film persistency in $H_2S$ environments. (These amounts relate to $CO_2$ and $H_2S$ environments, respectively.) When maleinized or fumarized fatty acids are used (with the same formulation of imidazoline/$O_2$ scavenger, etc.), these levels are reduced to 750 and 6,000 ppm, respectively. This effectively gives performance improvements over conventional dimer/trimer blends of approximately three to five fold depending upon the environment. This improvement is of both practical and economic value since it means that less handling of materials is needed and hence less cost is incurred at the operating well. Since this class of materials has been demonstrated to be of value in both sweet ($CO_2$) and sour ($H_2S$) environments, further ease and cost reduction are attained due to lower costs associated with inventory control.

DESCRIPTION OF THE PREFERRED EMBODIMENT(S)

The invention corrosion inhibitor is prepared from a suitable starting material containing unsaturated $C_{18}$ fatty acids. Any of the basic oils containing a significant amount of such fatty acids is a suitable starting material, including among others corn oil, cottonseed oil, lard, linseed oil, mustard seed oil, olive oil, palm oil, peanut oil, rapeseed oil, rice bran oil, safflower oil, sesame oil, sunflower oil, tallow, and whale oil. A preferred starting material is a mixture of tall oil fatty acids containing about 40-50% linoleic acid and 40-50% oleic/elaidic acid. Oleic and elaidic acids are the cis and trans forms, respectively, of the unsaturated $C_{18}$ fatty acid in tall oil. Typically, the amount of functionalized fatty acid is between 85 and 95% in such mixtures. A suitable amount of maleic anhydride is charged in the reaction apparatus (pressure reactor), and the material is heated for approximately two hours at 240° C. in the presence of iodine catalyst. This crude material, composed primarily of the Diels-Alder adduct of linoleic acid, is then distilled under suitable conditions to remove any unreacted fatty acid which is still present. The Diels-Alder adduct formation is taught in March, *Advanced Organic Chemistry, Reactions, Mechanism and Structure* (2nd ed. 1977), pp. 761-766, which teaching is incorporated herein by reference. In a subsequent step, the residual unreacted oleic/elaidic acid is treated, under more vigorous conditions, with additional maleic anhydride to form an ene adduct. The ene reaction and its product are taught in March, *Advanced Organic Chemistry, Reactions, Mechanism and Structure* (2nd ed. 1977), p. 726, which teaching is incorporated herein by reference. After both syntheses, removal of fatty acid is necessary. As with dimer/trimer mixes, the presence of such unreacted fatty acids has an adverse effect upon performance. Also, material obtained from the overheads of said removal steps (oleic/elaidic acids) can be maleinized in a subsequent step to produce product which is largely an ene adduct. This material may be backblended with the initial Diels-Alder adduct, or used as is, to give a similar acid anhydride which has identical performance characteristics. The reactions are performed sequentially to aid in processing and prevent thermal degradation of the Diels-Alder adduct. This material so obtained has a composition consisting of approximately 75 to 95% maleinized fatty acids, 15 to 20% thermal dimer (C-36) and trimer (C-54), and remaining unreacted fatty acid depending upon the relative proportions of the other constituents. Other constituents may be present in the purified material as well, such as esters, bis maleic anhydride adducts, and other types of species. These materials do not appear to qualitatively affect performance results and, therefore, are not routinely considered.

Testing procedures were performed in a wheel oven which provides for a constant temperature and rotation rate of sample bottles. This emulates downwell conditions with both oil and water environments and high temperatures. Normal testing procedures call for sparging sea salt solution and kerosene with $CO_2$ until saturated. For $H_2S$ environments the gas is generated from an $H_2S$ cylinder and titrated to a level of 500 ppm by an iodine/starch procedure. Metal coupons are then soaked in acetone, dried, and put into the testing bottles. The corrosion inhibitor formulation is then added. A typical corrosion inhibitor package will consist of 12.5 parts fatty acid derivative component, 12.5 parts of fatty acid imidazoline (e.g., Witcamine 209 or 211), one to two parts calcium dodecylbenzene sulfonate with the remainder being a heavy aromatic naptha solvent. The bottles are sparged for several minutes with $CO_2$ (In sour ($H_2S$) environments this is not done.), and equal amounts of kerosene and salt water are then added along with an oxygen scavenger (e.g., ammonium bisulfite). The bottles are then capped, put into a wheel oven and rotated through 360° to insure that each end of the metal coupon is exposed to both aqueous and oil environments. This treatment is done for one to two hours at 150° F., and then the coupons are removed and placed in a second set of bottles containing kerosene/salt water. These bottles are rotated for one hour; the coupons are removed a second time and again placed in a kerosene/salt water mixture and rotated at 150° F. for 22 hours to test for ultimate film persistency. After the treatment is complete, the metal coupons are removed from the bottles, rinsed in a 50/50:v/v:water/concentrated HCl mixture containing additional imidazoline, then rinsed in distilled water and finally isopropyl alcohol. After the rinsing is complete, the metal coupons are then dried by manual wiping. At this point they are then weighed, and the percent protection is reported according to the equation:

$$\% \text{ Protection} = \frac{A - B}{A} \times 100$$

A = Weight loss of blank coupons
B = Weight loss of inhibited coupons

Results for examples of maleinized and fumarized fatty acid derivatives and dimer/trimer mixes formulated in imidazoline environments are shown in Table I for sweet ($CO_2$) and sour ($H_2S$) environments, respectively. In all cases shown, the test results were obtained in a 50/50:v/v:oil/water environment. Here, we see that either maleinized linoleic or oleic acids, or a combination of both at a 50:50/w:w ratio gives material which gives excellent corrosion inhibition properties. In all cases, the percent inhibition was greater than 90%. It should be noted that in these tests the amount of protection which is considered desirable is 90% or greater. Inhibitors showing less than this value are not considered usable. Data indicate that either fumarized or maleinized linoleic acid and maleinized oleic acid can be used at levels of 750 ppm to give a protection (inhibition) of 92.5%. Mixing maleinized linoleic acid (or oleic) with 33% by weight Westvaco DTC-595, a dimer-trimer acid mixture (ca. 80% C-36 dimer acid and ca. 20% C-54 trimer acid), does not noticeably affect corrosion results; the percent inhibition remains at approximately 92%. Mixing in a two-thirds weight percentage of DTC-595 results in an inhibition level of approximately 66%, and employing DTC-595 alone results in a corrosion inhibition level of 33%. A similar pattern is noticed for both linoleic and oleic acids.

TABLE I

| Example No. | Material | % Inhibition @ 750 ppm[a] Sweet ($CO_2$) | % Inhibition @ 6000 ppm Sour ($H_2S$) |
|---|---|---|---|
| 1 | Fumarized Linoleic Acid | 92.5 | 95 |
| 2 | Maleinized Linoleic Acid | 92.5 | 95 |
| 3 | Maleinized Oleic Acid | 95.0 | 95 |
| 4 | 50/50:w/w Blend of Maleinized Linoleic and Oleic Acids | 95.0 | 95 |
| 5 | Maleinized Linoleic (Oleic) Acid Containing 33% by Weight DTC-595[b] | 92.2 | 98 |
| 6 | Maleinized Linoleic (Oleic) Acid Containing 50% by Weight DTC-595 | 76.0 | 95 |
| 7 | Maleinized Linoleic (Oleic) Acid Containing 66% by Weight DTC-595 | 66.5 | 75 |
| 8 | Dimer/Trimer Mixture (DTC-595) | 33.0 | 35 |

[a]Numbers are averages of several runs.
[b]DTC-595 - Westvaco product containing ca. 80% C-36 dimer acid and 20% C-54 trimer acid.

This series of results indicates that maleinized fatty acid is in fact the main agent giving the desired film persistency, and further, it may be used in blends of dimer/trimer acid to a certain extent and maintain the desired film persistency. Only at levels of ca. 40% or greater does the film persistency become seriously affected. Surprisingly, in $H_2S$ environments. Larger amounts of dimer/trimer acid may be tolerated in obtaining the required film persistency level of approximately 90% or greater. Dimer/trimer levels required under sweet conditions are in the 2000 to 3000 ppm range with no fatty acid anhydride present. This is uneconomic and causes problems in handling and storage, since approximately three times more material must be used. This problem is even more pronounced in wells which have a sour environment where approximately 30,000 ppm inhibitor is required if dimer/trimer mixes are used but only 6,000 ppm maleinized or fumarized fatty acid is required.

Under conditions which are frequently encountered downwell where the oil to water ratio in the produced fluids is less than 50:50, similar results are noted. A typical oil to water ratio is about 10 parts oil to 90 parts water. Under these conditions the amount of the corrosion inhibitor that is needed is generally less due to the fact that the inhibitor package is oil soluble. Results are shown in Tables II and III for sweet and sour film persistency, respectively.

TABLE II

| Film Persistency in 10:90/Oil:Water Media - Sweet | | | | | |
|---|---|---|---|---|---|
| Sweet Film | % Inhibition | | | | |
| Persistency (ppm) | Example 2 | Example 3 | Example 4 | Example 8 | Empol 1040 |
| 100 | 79.8 | 61.2 | 90.8 | — | 41.0 |
| 200 | 96.9 | 92.0 | 97.1 | — | 81.0 |
| 400 | 95.1 | 91.8 | 91.8 | — | 91.3 |
| 800 | 96.6 | 98.2 | 92.8 | 86.2 | 92.9 |
| 2000 | — | — | — | 96.7 | — |
| 4000 | — | — | — | 96.7 | — |

TABLE III

| Film Persistency in 10:90/Oil:Water Media - Sour | | | | | |
|---|---|---|---|---|---|
| Sour Film | % Inhibition | | | | |
| Persistency (ppm) | Example 2 | Example 3 | Example 4 | Example 8 | Empol 1040 |
| 300 | 82.2 | 84.1 | 83.5 | — | 49.6 |
| 500 | 91.9 | 87.9 | 89.4 | — | 62.0 |
| 1000 | 92.7 | 92.8 | 92.7 | — | 84.0 |
| 2000 | 93.1 | 94.2 | 92.9 | 83.8 | 91.5 |
| 20000 | — | — | — | 85.5 | — |
| 40000 | — | — | — | 89.1 | — |

Based on this data, it is apparent that maleinized fatty acids can be used in oil/water environments of 10/90 without any decrease in performance. Indeed, in sweet environments evidence indicates that the material is about four times better than dimer/trimer; in sour environments results show that a performance increase of tenfold or greater can be noted. Of further significance is the fact that the fatty acid anhydrides even outperform very high trimer (Empol 1040) materials. This is significant in that Empol 1040 is noted as an excellent material for film persistency, but is a byproduct of the dimer coatings industry. This has meant only sporadic supply of these materials. Our materials overcome any supply limitations by relying on readily available materials. Furthermore, we have demonstrated our ability to outperform these materials, available or not, further showing the value of this invention.

Therefore, a new oil field corrosion inhibitor has been discovered which can be used at considerably lower dosing levels than the commonly used dimer/trimer mixes. This factor enables economic savings and other incentives due to lower material handling costs, transportation costs, etc. In addition, the use of this material in conjunction with dimer/trimer materials also contents are no greater than 33% in sweet environments or 50% in sour environments under conditions of testing at 50/50:oil/water ratios.

What is claimed is:

1. A method for inhibiting corrosion in downwell oil field equipment and piping which is in contact with an oil/water medium taken from a producing well by coating said equipment and piping with a formulation including a reaction product of $C_{18}$ unsaturated fatty acids and a compound selected from the group consisting of maleic anhydride and fumaric acid, wherein said product is selected from the group consisting of a fatty acid Diels-Alder adduct and a fatty acid-ene reaction product, wherein the formulation is added to said oil/water medium.

2. The method of claim 1 wherein the fatty acids are selected from the group consisting of tall oil, olive oil, rapeseed oil, rice oil, tallow oil, whale oil, tung oil, corn oil, cottonseed oil, lard oil, and mustard seed oil.

3. The method of claim 2 wherein the tall oil fatty acids are selected from the group consisting of oleic acid, elaidic acid, and linoleic acid.

4. The method of claim 1 wherein the formulation includes an imidazoline base.

5. The method of claim 4 wherein the formulation includes between 0.5% and 99.5% reaction product, by weight, and between 99.5% and 0.5% imidazoline base, by weight.

6. The method of claim 5 wherein the formulation includes between 5% and 25% reaction product, by weight, and between 95% and 75% imidazoline base, by weight.

7. The method of claim 4 wherein the formulation includes between 0.5% and 90% of a dimer acid-trimer acid blend, based on the weight of the reaction product.

8. The method of claim 1 wherein the formulation includes up to 20% unreacted fatty acid, based on weight.

9. The method of claim 4 wherein the imidazoline base has a chain length from 2 to 26 carbons.

* * * * *